US012077827B2

(12) United States Patent
Hery-Arnaud et al.

(10) Patent No.: US 12,077,827 B2
(45) Date of Patent: Sep. 3, 2024

(54) METHODS FOR PREDICTING THE RISK OF DEVELOPING PULMONARY COLONIZATION/INFECTION BY *Pseudomonas aeruginosa*

(71) Applicants: INSERM (INSTITUT NATIONAL DE LA SANTÉ ET DE LA RECHERCHE MÉDICALE), Paris (FR); UNIVERSITÉ DE BRETAGNE OCCIDENTALE, Brest (FR); ETABLISSEMENT FRANCAIS DU SANG (EFS), La Plaine Saint Denis (FR); CENTRE HOSPITALIER REGIONSL ET UNIVERSITAIRE DE BREST, Brest (FR); INSTITUT NATIONAL DE RECHERCHE POUR L'AGRICULTURE, L'ALIMENTATION ET L'ENVIRONNEMENT, Paris (FR)

(72) Inventors: Geneviève Hery-Arnaud, Brest (FR); Jérôme Mounier, Plouzané (FR); Marlène Keravec, Plouzané (FR); Stanislas Mondot, Jouy-en-Josas (FR); Patricia Lepage, Jouy-en-Josas (FR); Charles-Antoine Guilloux, Brest (FR)

(73) Assignees: INSERM (INSTITUT NATIONAL DE LA SANTE ET DE LA RECHERCHE MEDICALE), Paris (FR); UNIVERSITE DE BRETAGNE OCCIDENTALE, Brest (FR); ETABLISSEMENT FRANCAIS DU SANG (EFS), La Plaine Saint Denis (FR); CENTRE HOSPITALIER REGIONAL ET UNIVERSITAIRE DE BREST, Brest (FR); INSTITUT NATIONAL DE RECHERCHE POUR L'AGRICULTURE, L'ALIMENTATION ET L'EVIRONNEMENT, Paris (FR)

( * ) Notice: Subject to any disclaimer, the term of this patent is extended or adjusted under 35 U.S.C. 154(b) by 307 days.

(21) Appl. No.: 16/651,426

(22) PCT Filed: Sep. 28, 2018

(86) PCT No.: PCT/EP2018/076442
§ 371 (c)(1),
(2) Date: Mar. 27, 2020

(87) PCT Pub. No.: WO2019/063783
PCT Pub. Date: Apr. 4, 2019

(65) Prior Publication Data
US 2020/0283829 A1 Sep. 10, 2020

(30) Foreign Application Priority Data
Sep. 29, 2017 (EP) .................... 17306297
Dec. 7, 2017 (EP) .................... 17306717

(51) Int. Cl.
| | |
|---|---|
| C12Q 1/68 | (2018.01) |
| A61K 35/741 | (2015.01) |
| C07K 16/12 | (2006.01) |
| C12Q 1/689 | (2018.01) |
| A61K 35/00 | (2006.01) |
| A61K 45/06 | (2006.01) |

(52) U.S. Cl.
CPC ............ C12Q 1/689 (2013.01); A61K 35/741 (2013.01); C07K 16/1214 (2013.01); *A61K 2035/115* (2013.01); *A61K 45/06* (2013.01); *C12Q 2600/118* (2013.01); *G01N 2800/12* (2013.01); *G01N 2800/50* (2013.01)

(58) Field of Classification Search
None
See application file for complete search history.

(56) References Cited

FOREIGN PATENT DOCUMENTS

| CA | 2 606 828 A1 | 5/2009 |
|---|---|---|
| WO | 2002/064161 A2 | 8/2002 |

OTHER PUBLICATIONS

Guss et al. The ISME Journal (2011) 5, 20-29 (Year: 2015).*
Van der Gast The ISME Journal (2011) 5, 780-791 (Year: 2011).*
Van Biervliet Clinical Nutrition ESPEN 18 (2017) 37e43, pp. 1-7 (Year: 2017).*
Anad et al. (2018) Diet, Microbiota and Gut-Lung Connection. Front. Microbiol. 9:2147, p. 1-12 (Year: 2018).*
Price CE, O'Toole GA. 2021. The gutlung axis in cystic fibrosis. J Bacteriol 203: e00311-21. https://doi.org/10.1128/JB.00311-21, pp. 1-26 (Year: 2021).*
Li et al. (Microbes and Infection 16 (2014) 17e27) (Year: 2014).*
Brook (J. Med. Microbiol.—vol. 42 (1995), 340-347) (Year: 1995).*
Keravec et al. (WS07.3 (Jun. 2016) vol. 15, Supp. Supplement 1, pp. S11. Abstract No. WS07.3. Meeting Info: 39th European Cystic Fibrosis Conference. Basel, Switzerland. Jun. 8, 2016-Jun. 11, 2016 ISSN: 1873-5010 (Year: 2016).*
Cuthbertson et al. (The ISME Journal (2016) 10, 1081-1091) (Year: 2016).*
Frederiksen et al. (Pediatric Pulmonology 23:330-335 (1997)) (Year: 1997).*

(Continued)

*Primary Examiner* — Juliet C Switzer
(74) *Attorney, Agent, or Firm* — WC&F IP

(57) ABSTRACT

The present invention relates to methods for predicting the risk of developing pulmonary colonization/infection by *P. aeruginosa*. The inventors analyzed the respiratory tract microbiota from 65 patients sputum samples and compared microbiota data. The inventors found that patients that will remain uninfected from *P. aeruginosa* exhibited 3-fold higher abundance of *Porphyromonas* compared to the other groups. In particular, the present invention relates to a method for predicting the risk of developing pulmonary colonization/infection by *P. aeruginosa* in a subject suffering from cystic fibrosis (CF) comprising measuring the abundance of *Porphyromonas* genus bacteria in a biological sample obtained from said subject.

4 Claims, 4 Drawing Sheets

(56) References Cited

OTHER PUBLICATIONS

Figure 1:
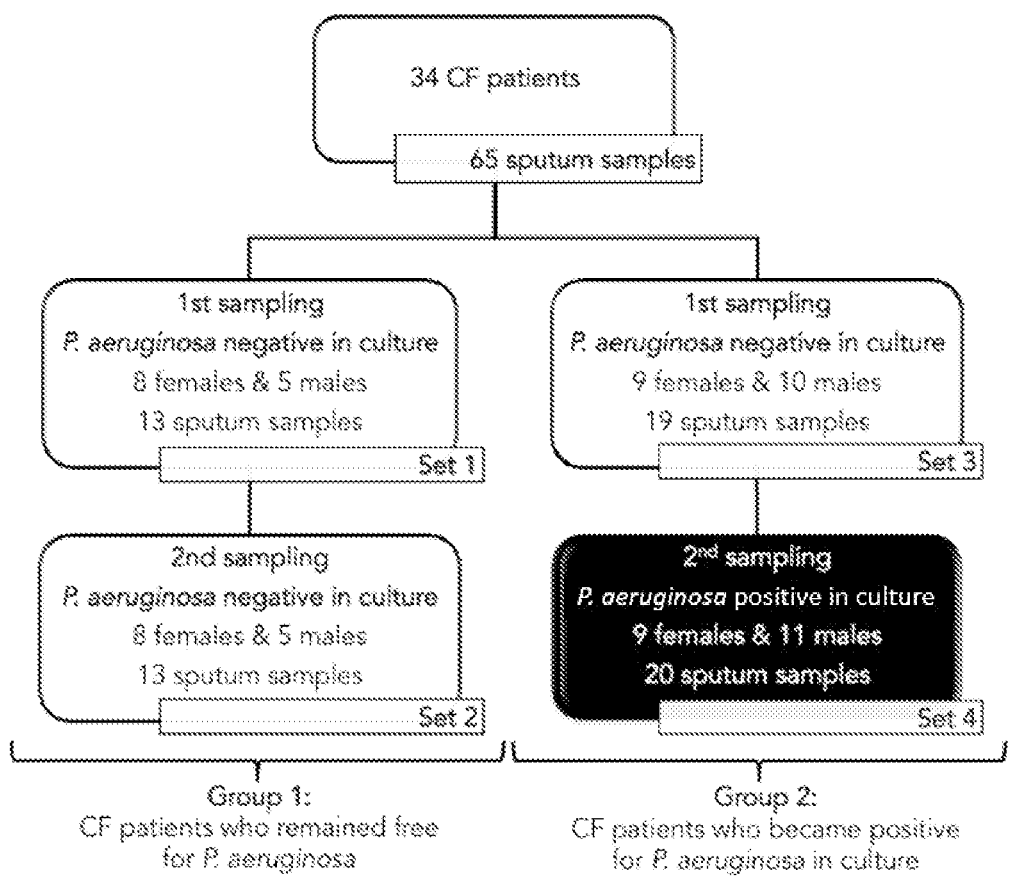

Coburn et al. (May 2015, Scientific Reports, 5:10241, DOI: 10.1038/srep10241, 12 pages (Year: 2015).*

Abman et al: "Early bacteriologic, immunologic, and clinical course of young infants with cystic fibrosis identified by neonatal screening", The Jouranl of Padiatrics, vol. 119, No. 2, pp. 211-217, Aug. 1, 1991.

Coburn et al: "Lung microbiota across age and disease stage in cystic fibrosis", Scientific Reports, vol. 5, No. 1, May 14, 2015.

Maselli et al: "Risk factors for initial acquisition of *Pseudomonas aeruginosa* in children with cystic fibrosis identified by newborn screening", Pediatric Pulmonology, vol. 35, No. 4, pp. 257-262, Apr. 1, 2003.

* cited by examiner

METHODS FOR PREDICTING THE RISK OF DEVELOPING PULMONARY COLONIZATION/INFECTION BY *Pseudomonas aeruginosa*

FIELD OF THE INVENTION

The present invention relates to methods for predicting the risk of developing pulmonary colonization/infection by *Pseudomonas aeruginosa*.

BACKGROUND OF THE INVENTION

Respiratory polymicrobial infections play a major role in cystic fibrosis (CF) progression and the acquisition of bacterial pathogens during the course of the disease is now well described. Indeed, the CF pulmonary microbiota is typically dominated either by *Haemophilus influenzae* or *P. aeruginosa* (Rogers G B, van der Gast C, Serisier D J (2015) Predominant pathogen competition and core microbiota divergence in chronic airway infection. ISME J 9:217-225). *P. aeruginosa* has a negative impact on pulmonary function promoting more frequent acute exacerbations (Rosenfeld M, Ramsey B W, Gibson R L (2003) *Pseudomonas* acquisition in young patients with cystic fibrosis: pathophysiology, diagnosis, and management. Curr Opin Pulm Med 9(6):492-497). After ~25 years old, the establishment of CF pathogens is usually completed, *P. aeruginosa* being the most predominant species in CF lung (Coburn B, Wang P W, Diaz Caballero J, Clark S T, Brahma V, Donaldson S, Zhang Y, Surendra A, Gong Y, Tullis D E, Yau Y C W, Waters V J, Hwang D M, Guttman D S (2015) Lung microbiota across age and disease stage in cystic fibrosis. Sci rep 5:10241). *P. aeruginosa* colonization is considered as a crucial turning-point in the disease course of CF patients.

The current challenge is to decipher the factors involved in this turning point. Demographic and environmental actors were shown to increase the risk of *P. aeruginosa* acquisition (Maselli J H, Sontag M K, Norris J M, MacKenzie T, Wagener J S, Accurso F J (2003) Risk factors for initial acquisition of *P. aeruginosa* in children with cystic fibrosis identified by newborn screening. Pediatr pulmonol 35(4):257-262). A large proportion of anaerobic bacteria such as *Prevotella* and *Veillonella* have also been detected in CF sputum samples, and presumed to act detrimentally on respiratory function (Zhao J, Schloss P D, Kalikin L M, Carmody L A, Foster B K, Petrosino J F, Cavalcoli J D, Van Devanter D R, Murray S, Li J Z, Young V B, LiPuma J J (2012) Decade-long bacterial community dynamics in cystic fibrosis airways. Proc Natl Acad Sci USA 109(15):5809-5814). Besides bacteria, fungi and viruses colonize the upper and lower pulmonary tract of CF patients (Wat D, Gelder C, Hibbitts S, Cafferty F, Bowler I, Pierrepoint M, Evans R, Doull I (2008) The role of respiratory viruses in cystic fibrosis. J Cyst Fibros 7(4):320-328) (Mounier J, Gouëllo A, Keravec M, Le Gal S, Pacini G, Debaets S, Nevez G, Rault G, Barbier G, Héry-Arnaud G (2014) Use of denaturing high-performance liquid chromatography (DHPLC) to characterize the bacterial and fungal airway microbiota of cystic fibrosis patients. J Microbiol 52(4):307-314), and may play a key role in its pathogenesis.

SUMMARY OF THE INVENTION

The present invention relates to methods for predicting the risk of developing pulmonary colonization/infection by *P. aeruginosa*. In particular, the present invention is defined by the claims.

DETAILED DESCRIPTION OF THE INVENTION

The objective of the inventors was to identify predictive biomarkers of *P. aeruginosa* colonization/infection.

For 88 months, thirty-four CF patients (mostly children) were followed and divided into 2 groups; one group infected by *P. aeruginosa* during the follow-up, and the other group, which remained uninfected. The respiratory tract microbiota from 65 sputum samples was analyzed through 16S rRNA gene sequencing and RT-PCR screening of 18 respiratory viruses, taking into account potential host factors involved in the lung disease progression. The inventors compared microbiota data between the two groups of patients. They additionally investigated the presence of 'pulmotypes' across the CF cohort. Multiple statistical approaches were conducted and clustering strength was tested.

*Porphyromonas* genus (*P. catoniae* and *P. endodontalis*), as enriched phylotypes in patients uninfected by *P. aeruginosa* (p-value<0.001), was biomarker of a non-permissive airway microbiota.

In the personalized medicine era, the inventors intended to find biomarkers for providing a close monitoring to CF patients more at risk of early *P. aeruginosa* colonization/infection, and improving clinical benefit of successfully early *P. aeruginosa* eradication.

Accordingly, a first aspect of the present invention relates to a method for predicting the risk of developing pulmonary colonization/infection by *P. aeruginosa* in a subject suffering from cystic fibrosis (CF) comprising:

Measuring the abundance of *Porphyromonas* genus bacteria in a biological sample obtained from said subject;

Concluding that the subject has a low risk of developing *P. aeruginosa* pulmonary colonization/infection when an elevated abundance of *Porphyromonas* genus bacteria is measured or concluding that the subject has a high risk of developing *P. aeruginosa* pulmonary colonization/infection when a low abundance of *Porphyromonas* genus bacteria is measured.

As used herein, the term cystic fibrosis (CF) has its general meaning in the art and refers to an inherited condition that affects various parts of the body, particularly the lungs but also the pancreas, liver, kidneys, and intestine. Long-term issues include difficulty breathing as a result of frequent lung infections. Other signs and symptoms may include sinus infections, poor growth, fatty stool, clubbing of the fingers and toes, and infertility in males. Cystic fibrosis (CF) is the most common severe autosomal recessive genetic disorder in the Caucasian population.

As used herein, the term "pulmonary colonization/infection by *P. aeruginosa*" relates to any infectious disease involving the lungs caused by *P. aeruginosa*.

As used herein, the term "*P. aeruginosa*" has its general meaning in the art and refers to a common Gram-negative, rod-shaped bacterium.

As used herein, the term "*Porphyromonas* genus" has its general meaning in the art and refers to a Gram-negative, non-spore-forming, anaerobic and non-motile genus from the family of Porphyromonadaceae, which is recognized as a separate taxon on the basis of ribosomal DNA homology and 16S rRNA data.

As used herein, the term "abundance" refers to the quantity or the concentration of said bacteria in a location/sample.

In one embodiment, the abundance is absolute abundance.

As used herein, the term "absolute abundance" refers to the concentration of said bacteria in a location/sample expressed for instance in number of UFC per mL or genome equivalent per mL.

In one embodiment, the abundance is relative abundance.

As used herein, the term "relative abundance" refers to the percent composition of a bacterium genus relative to the total number of bacteria genus in a given location/sample.

As used herein, the term "subject" denotes a mammal. In a preferred embodiment of the invention, a subject according to the invention refers to any subject (preferably human) afflicted or at risk to be afflicted with cystic fibrosis. The method of the invention may be performed for any type of cystic fibrosis such as revised in the World Health Organisation Classification of cystic fibrosis and selected from the E84 group: mucoviscidosis, Cystic fibrosis with pulmonary manifestations, Cystic fibrosis with intestinal manifestations and Cystic fibrosis with other manifestations.

In one embodiment, the subject is a newborn.

In one embodiment, the subject is a child. In one embodiment, the age of the child is inferior to 12 months.

In one embodiment, the subject is an adult.

As used herein, the term "biological sample" is used herein in its broadest sense. A biological sample is generally obtained from a subject. A sample may be of any biological tissue or fluid with which biomarker of the present invention may be assayed. Frequently, a sample will be a "clinical sample", i.e., a sample derived from a patient. Such samples include, but are not limited to, bodily fluids which may or may not contain cells, e.g., blood (e.g., whole blood, serum or plasma), synovial fluid, saliva, tissue or fine needle biopsy samples, and archival samples with known diagnosis, treatment and/or outcome history. Biological samples may also include sections of tissues such as frozen sections taken for histological purposes. The term "biological sample" also encompasses any material derived by processing a biological sample. Derived materials include, but are not limited to, cells (or their progeny) isolated from the sample, or proteins, DNA or RNA extracted from the sample.

In one embodiment, the biological sample is bronchoalveolar lavage (BAL) or sputum or protected specimen brushing (from bronchoscopic sampling) or pharyngeal swabs. In one embodiment, the biological sample is spontaneous or induced sputum samples.

As used herein, the term "predicting" refers to a probability or likelihood for a subject to develop an event. Preferably, the event is herein broncho-pulmonary colonization/infection by *P. aeruginosa*.

As used herein, the term "risk" refers to the probability that an event will occur over a specific time period, such as the onset of pulmonary colonization/infection by *P. aeruginosa*, and can mean a subject's "absolute" risk or "relative" risk. Absolute risk can be measured with reference to either actual observation post-measurement for the relevant time cohort, or with reference to index values developed from statistically valid historical cohorts that have been followed for the relevant time period. Relative risk refers to the ratio of absolute risks of a patient compared either to the absolute risks of low risk cohorts or an average population risk, which can vary by how clinical risk factors are assessed.

According to the method of the invention, the abundance of *Porphyromonas* genus bacteria is measuring. All the methods for measuring the abundance known by the skilled man may be used. Examples of these methods include but not limited to direct microscopic counts, electronic counting chambers, indirect viable cell counts, cultivation-based techniques or molecular methods.

In one embodiment, the abundance of *Porphyromonas* genus bacteria is measuring by any routine method well known in the art and typically by using molecular methods. In one embodiment, the abundance of *Porphyromonas* genus bacteria is measuring using 16S rRNA deep-sequencing. In one embodiment, the abundance of *Porphyromonas* genus bacteria is measuring using the abundance table generated by the next-generation sequencing of 16S rRNA genes of all bacteria within a given biological sample using qPCR technique. Nucleic acids may be extracted from a sample by routine techniques such as those described in Diagnostic Molecular Microbiology: Principles and Applications (Persing et al. (eds), 1993, American Society for Microbiology, Washington D.C.). U.S. Pat. Nos. 4,683,202, 4,683,195, 4,800,159, and 4,965,188 disclose conventional PCR techniques. PCR typically employs two oligonucleotide primers that bind to a selected target nucleic acid sequence. Primers useful in the present invention include oligonucleotides capable of acting as a point of initiation of nucleic acid synthesis within the target nucleic acid sequence. qPCR involves use of a thermostable polymerase. The term "thermostable polymerase" refers to a polymerase enzyme that is heat stable, i.e., the enzyme catalyzes the formation of primer extension products complementary to a template and does not irreversibly denature when subjected to the elevated temperatures for the time necessary to effect denaturation of double-stranded template nucleic acids. Generally, the synthesis is initiated at the 3' end of each primer and proceeds in the 5' to 3' direction along the template strand. Thermostable polymerases have been isolated from *Thermus fiavus, T. ruber, T. thermophilus, T. aquaticus, T. lacteus, T. rubens, Bacillus stearothermophilus,* and *Methanothermus fervidus*. Nonetheless, polymerases that are not thermostable also can be employed in PCR assays provided the enzyme is replenished. Typically, the polymerase is a Taq polymerase (i.e. *Thermus aquaticus* polymerase). The primers are combined with PCR reagents under reaction conditions that induce primer extension. The newly synthesized strands form a double-stranded molecule that can be used in the succeeding steps of the reaction. The steps of strand separation, annealing, and elongation can be repeated as often as needed to produce the desired quantity of amplification products corresponding to the target nucleic acid sequence molecule. The limiting factors in the reaction are the amounts of primers, thermostable enzyme, and nucleoside triphosphates present in the reaction. The cycling steps (i.e., denaturation, annealing, and extension) are preferably repeated at least once. For use in detection, the number of cycling steps will depend, e.g., on the nature of the sample. If the sample is a complex mixture of nucleic acids, more cycling steps will be required to amplify the target sequence sufficient for detection. Generally, the cycling steps are repeated at least about 20 times, but may be repeated as many as 40, 60, or even 100 times.

The 16S deep-sequencing technique is well-described in the state of the art for instance, Shendure and Ji. "Next-generation DNA sequencing", Nature Biotechnology, 26(10):1135-1145 (2008)).

The 16S deep-sequencing technique also known as "next-generation DNA sequencing" ("NGS"), "high-throughput sequencing", "massively parallel sequencing" and "deep sequencing" refers to a method of sequencing a plurality of nucleic acids in parallel. See e.g., Bentley et al, Nature 2008, 456:53-59. The leading commercially available platforms produced by Roche/454 (Margulies et al, 2005a), Illumina/Solexa (Bentley et al, 2008), Life/APG (SOLiD) (McKernan et al, 2009) and Pacific Biosciences (Eid et al, 2009) may be used for deep sequencing. For example, in the 454 method, the DNA to be sequenced is either fractionated and supplied with adaptors or segments of DNA can be PCR-amplified using primers containing the adaptors. The adaptors are nucleotide 25-mers required for binding to the DNA Capture Beads and for annealing the emulsion PCR Amplification Primers and the Sequencing Primer. The DNA fragments are made single stranded and are attached to DNA capture beads in a manner that allows only one DNA fragment to be attached to one bead. Next, the DNA containing beads are emulsified in a water-in-oil mixture resulting in microreactors containing just one bead. Within the microreactor, the fragment is PCR-amplified, resulting in a copy number of several million per bead. After PCR, the emulsion is broken and the beads are loaded onto a pico titer plate. Each well of the pico-titer plate can contain only one bead. Sequencing enzymes are added to the wells and nucleotides are flowed across the wells in a fixed order. The incorporation of a nucleotide results in the release of a pyrophosphate, which catalyzes a reaction leading to a chemiluminescent signal. This signal is recorded by a CCD camera and a software is used to translate the signals into a DNA sequence. In the Illumina method (Bentley (2008)), single stranded, adaptor-supplied fragments are attached to an optically transparent surface and subjected to "bridge amplification". This procedure results in several million clusters, each containing copies of a unique DNA fragment. DNA polymerase, primers and four labeled reversible terminator nucleotides are added and the surface is imaged by laser fluorescence to determine the location and nature of the labels. Protecting groups are then removed and the process is repeated for several cycles. The SOLiD process (Shendure (2005)) is similar to 454 sequencing, DNA fragments are amplified on the surface of beads. Sequencing involves cycles of ligation and detection of labeled probes. Several other techniques for high-throughput sequencing are currently being developed. Examples of such are The Helicos system (Harris (2008)), Complete Genomics (Drmanac (2010)) and Pacific Biosciences (Lundquist (2008)). As this is an extremely rapidly developing technical field, the applicability to the present invention of high throughput sequencing methods will be obvious to a person skilled in the art.

A further object of the present invention relates to a method of preventing pulmonary colonization/infection by *P. aeruginosa* in a subject suffering from cystic fibrosis (CF) comprising:

Predicting the risk of developing pulmonary colonization/infection by *P. aeruginosa* by using the method of the present invention;

Administering to the subject a therapeutically effective amount of *P. aeruginosa* specific antibiotics when it is concluded that the subject has a high risk of developing *P. aeruginosa* pulmonary colonization/infection.

In one embodiment, *P. aeruginosa* specific antibiotics are aminoglycosides (gentamicin, amikacin, tobramycin, but not kanamycin).

In one embodiment, *P. aeruginosa* specific antibiotics are quinolones (ciprofloxacin, levofloxacin, but not moxifloxacin).

In one embodiment, *P. aeruginosa* specific antibiotics are cephalosporins (ceftazidime, cefepime, cefoperazone, cefpirome, ceftobiprole, but not cefuroxime, cefotaxime, or ceftriaxone).

In one embodiment, *P. aeruginosa* specific antibiotics are ceftazidime-avibactam or ceftolozane-tazobactam.

In one embodiment, *P. aeruginosa* specific antibiotics are antipseudomonal penicillins: carboxypenicillins (carbenicillin and ticarcillin), and ureidopenicillins (mezlocillin, azlocillin, and piperacillin).

In one embodiment, *P. aeruginosa* specific antibiotics are carbapenems (meropenem, imipenem, doripenem, but not ertapenem).

In one embodiment, *P. aeruginosa* specific antibiotics are polymyxins (polymyxin B and colistin).

In one embodiment, *P. aeruginosa* specific antibiotics are monobactams (aztreonam).

In a preferred embodiment, *P. aeruginosa* specific antibiotics are ciprofloxacine per os and inhaled colistin.

In a preferred embodiment, *P. aeruginosa* specific antibiotics are inhaled tobramycine.

A further object of the present invention relates to a method of preventing pulmonary colonization/infection by *P. aeruginosa* in a subject suffering from cystic fibrosis (CF) comprising:

Predicting the risk of developing pulmonary colonization/infection by *P. aeruginosa* by using the method of the present invention;

Administering to the subject a therapeutically effective amount of *Porphyromonas* probiotics when it is concluded that the subject has a high risk of developing *P. aeruginosa* pulmonary colonization/infection.

As used herein, the term "preventing" refers to the reduction in the risk of acquiring or developing a given condition.

As used herein, the term "probiotic" refers to a live microorganism which when administered in adequate therapeutic amounts confer a health benefit on a subject. Health benefits are a result of production of nutrients and/or co-factors by the probiotic, competition of the probiotic with pathogens and/or stimulation of an immune response in the subject by the probiotic.

The terms "administer" or "administration" refer to the act of injecting or otherwise physically delivering a substance as it exists outside the body into the subject, such as by mucosal, intradermal, intravenous, subcutaneous, intramuscular, intra-articular delivery and/or any other method of physical delivery described herein or known in the art. When a disease, or a symptom thereof, is being treated, administration of the substance typically occurs after the onset of the disease or symptoms thereof. When a disease or symptoms thereof, are being prevented, administration of the substance typically occurs before the onset of the disease or symptoms thereof.

By a "therapeutically effective amount" is meant a sufficient amount of *P. aeruginosa* specific antibiotics for use in a method for the prevention of pulmonary colonization/infection by *P. aeruginosa* at a reasonable benefit/risk ratio applicable to any medical treatment. It will be understood that the total daily usage of the compounds and compositions of the present invention will be decided by the attending physician within the scope of sound medical judgment. The specific therapeutically effective dose level for any particular subject will depend upon a variety of factors including the age, body weight, general health, sex and diet of the subject; the time of administration, route of administration, and rate of excretion of the specific compound employed; the duration of the treatment; and like factors well known in the medical arts. For example, it is well known within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Typically, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, typically from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

Another object of the present invention relates to a method of adjusting the patient monitoring, said method comprising:

Predicting the risk of developing pulmonary colonization/infection by *P. aeruginosa* by using the method of the present invention;

Increasing the frequency of medical check-up when it is concluded that the subject has a high risk of developing *P. aeruginosa* pulmonary colonization/infection.

For instance, the medical check-up may be carried out every month or every 15 days when it is concluded that the subject has a high risk of developing *P. aeruginosa* pulmonary colonization/infection whereas a standard patient monitoring comprises a medical check-up every three-months.

In order to confirm the prediction of the risk of developing pulmonary colonization/infection by *P. aeruginosa* in a subject suffering from cystic fibrosis obtained using the method of the invention, it is possible to detect *P. aeruginosa* by qPCR (Hery-Arnaud et al., CMI 2017: qPCR provides a window of opportunity of 8 months).

Another object of the present invention relates to a method for stratifying subject suffering from cystic fibrosis, wherein said method comprises:

Determining the bacterium species the more abundant in the respiratory tract of said subject;

Concluding to a favorable cystic fibrosis progression when the bacterium species the more abundant in the respiratory tract of said subject is *Streptococcus* or *Haemophilus*, or concluding to an unfavorable cystic fibrosis progression when the bacterium species the more abundant in the respiratory tract of said subject is *Staphylococcus*.

Another object of the present invention relates to a method for predicting the risk of developing pulmonary colonization/infection by *P. aeruginosa* in a subject suffering from cystic fibrosis (CF) comprising:

Detecting the presence or the absence of rhinovirus in the respiratory tract of said subject;

Concluding that the subject has a low risk of developing *P. aeruginosa* pulmonary colonization/infection when the presence of rhinovirus is detected or concluding that the subject has a high risk of developing *P. aeruginosa* pulmonary colonization/infection when the absence of rhinovirus is detected.

Another object of the present invention relates to a method for predicting the risk of developing pulmonary colonization/infection by *P. aeruginosa* in a subject suffering from cystic fibrosis (CF) comprising:

Determining the bacterium species the more abundant in the respiratory tract of said subject;

Concluding that the subject has a low risk of developing *P. aeruginosa* pulmonary colonization/infection when the bacterium species the more abundant in the respiratory tract of said subject is *Streptococcus* or *Haemophilus*, or concluding that the subject has a high risk of developing *P. aeruginosa* pulmonary colonization/infection when the bacterium species the more abundant in the respiratory tract of said subject is *Staphylococcus*.

The invention will be further illustrated by the following figures and examples. However, these examples and figures should not be interpreted in any way as limiting the scope of the present invention.

FIGURES

FIG. 1: Design of the study.

FIG. 2: a) Normalized abundance of *P. aeruginosa* in each set. b) Normalized abundance of *Porphyromonas* in each group. c) Results of random forest analysis showing the 15 taxa that contributed the most to each group based on the measure of mean decrease in accuracy.

EXAMPLE

Material & Methods

Patient Cohort, Inclusion Criteria and Global Data.

In the present study, 34 CF patients (17 females and 17 males) with a median age of 13.8 years ([IQR: 7.8-31 years]) were included and followed-up for a period of 8 months in median [IQR: 1-23 months]. CF patients were categorized as 'free' and 'never' based on the Lee's criteria, which define the *P. aeruginosa* infection status of the patient for the $1^{st}$ sampling. Other clinical and biological data collected at each sampling time were collected, including: age, sex, CFTR mutation, clinical state according to the four stages defined by Price et al. (baseline, exacerbation, treatment, or recovery) (DOI: 10.1186/2049-2618-1-27), antibiotic treatment, BMI, Lee'status (DOI: 10.1016/S1569-1993(02)00141-8), and quality of sputum samples (scoring established according to cytological parameters, epithelial cells and leukocytes). The analysis of pulmonary bacterial and viral communities was performed on spontaneous sputum samples collected at 2 time points: at enrollment (time point 0) and after 8 months in median (FIG. 1). At the end of the follow-up, patients divided to two groups. Group 1 ("contained patients who remained free of *P. aeruginosa* while patients from group 2 became positive in culture for *P. aeruginosa* during the follow-up (FIG. 1).

Nucleic Acid Extraction from Sputum Samples.

For bacterial composition assessment, total DNA was extracted using the QIAamp DNA Mini Kit (QIAGEN, Courtaboeuf, France). Viral RNA and DNA were extracted from the same sputum samples using the NUCLISENS® easyMAG™ automated extractor (bioMérieux, Marcy l'Etoile, France) after treatment with 25 µl of proteinase K (10 mg/ml) for 4 h at 56° C.

Bacterial Microbiota Description.

Barcoded high-throughput 454 pyrosequencing was performed on the amplified V3 and V4 hypervariable regions of the 16S rRNA gene (Bioproject PRJNA 297396).

Screening of Respiratory Viruses.

The RespiFinder® SMART 22 FAST kit (PathoFinder, Maastricht, The Netherlands) was used in a GeneAmp® PCR System 9700 (Applied Biosystems, Courtaboeuf, France) to simultaneously detect 18 human respiratory viruses. Moreover, a specific qPCR was performed to discriminate both HRV and HEV.

Bioinformatic and Statistical Analyses.

Sequences were analyzed with the standard UPARSE pipeline. A significance threshold of 0.05 was set for all statistical analyses. The false discovery rate (FDR) was calculated to correct for multiple hypothesis testing.

Results
Global Composition of the Airway Microbiota in Cystic Fibrosis.
Bacterial Communities.

Five predominant phyla, i.e., Firmicutes (43.11%), Proteobacteria (32.18%), Bacteroidetes (13.31%), Actinobacteria (7.66%) and Fusobacteria (3.62%) were found and eleven predominant genera (relative abundance≥1%) were found, namely, *Streptococcus* (22.73%), *Haemophilus* (14.80%), *Staphylococcus* (10.66%), *Neisseria* (10.19%), *Prevotella* (7.57%), *Rothia* (7.01%), *Porphyromonas* (5.33%), *Veillonella* (4.14%), *Fusobacterium* (2.98%), *Granulicatella* (1.74%) and *Pseudomonas* (1.26%). Only 1 OTU assigned to the *Streptococcus mitis* group was shared among all samples.

Viral Communities.

Respiratory viruses were detected in 29.2% of sputum samples (n=19). Viral co-infection (≥2 viruses) was observed in 4.6% of sputum samples (n=3). HRV/HEV were the most prevalent viruses as they were detected in 24.6% of samples (HRV, n=7; HEV, n=9). Adenovirus, Parainfluenza 2, Coronavirus 229E and NL63 were detected in 4.6% (n=3), 3.1% (n=2), 1.5% (n=1) and 1.5% (n=1), respectively. There was no significant correlation between the presence of rhinovirus and/or non-rhinovirus and pulmonary exacerbation.

Effect of Gender.

Estimated and observed bacterial species richness as well as diversity were significantly greater in male patients (observed species: 54.07±18.4; H': 3.4±1.04) than in female patients (observed species: 43.78±16.4; H': 2.8±0.95). For both male and female cohorts, patient's age did not explain this difference (t-test, p-value>0.5). Furthermore, the composition of the CF pulmonary microbiota varied according to the gender as revealed by Unifrac weighted analysis (adonis test; p<0.05). Relative abundances (RA) of *Selenomonas*, *Leptotrichia*, *Parvimonas* and *Atopobium* were significantly more important (Mann-Whitney test, p-value<0.05) in the male group with a M/F sex ratio of 3.3, 3.1, 15.8 and 6.2, respectively; while *Bifidobacterium* was only found (at low abundance, RA<0.1%) in the male group. Moreover, *Parvimonas* was significantly more abundant in male patients who remained uninfected during the follow-up (Mann-Whitney test, p-value=001). Samples were classified with a 0.24+/−0.08 error rate, which is 2 times higher than the baseline error rate for random guessing (0.49).

Investigation of Biomarkers Associated to a Lower Risk of Early *P. aeruginosa* Colonization.

In patients from group 2, bacterial diversity was similar before and colonization by *P. aeruginosa*. Diversity was also not modified overtime in patients from group 1.

*Porphyromonas*, a Key Genus.

Figure 2A:
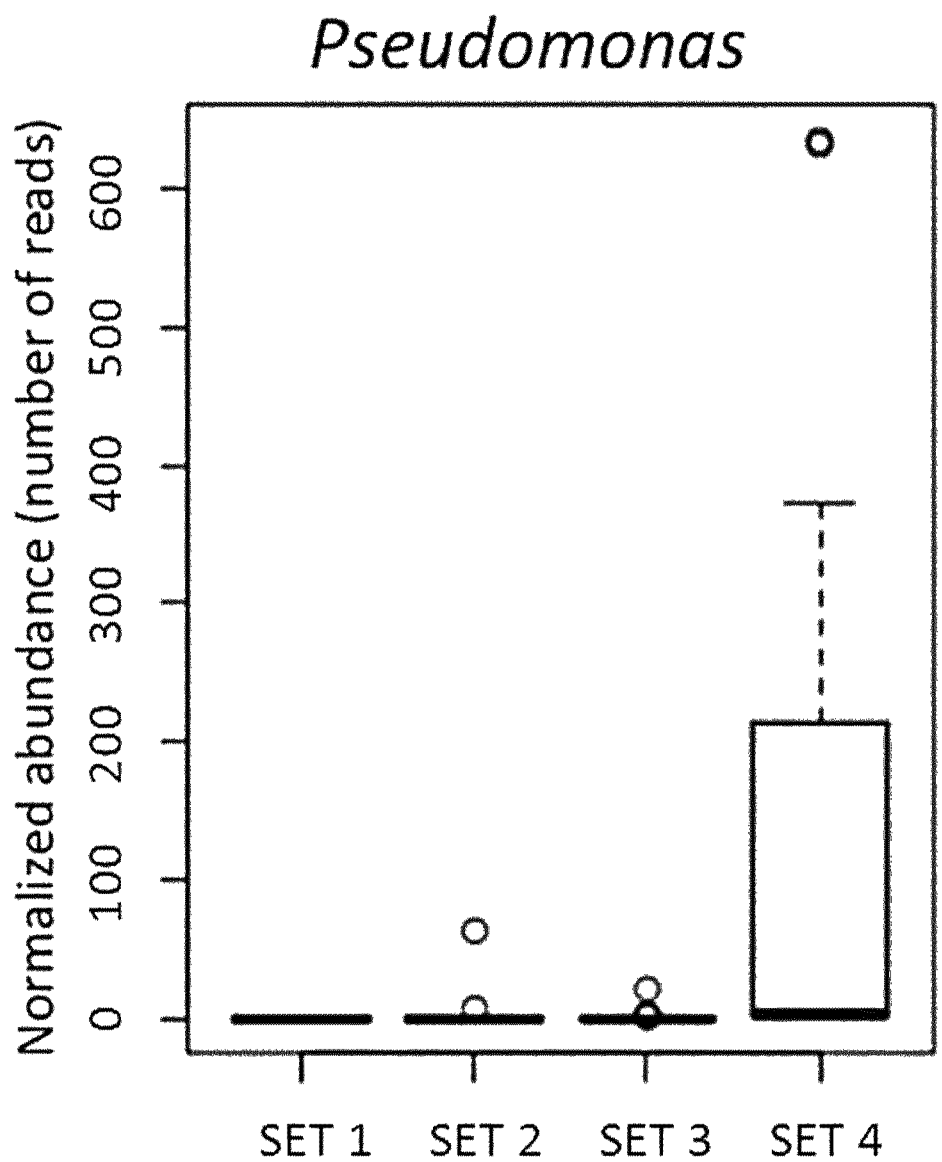
Figure 2B:
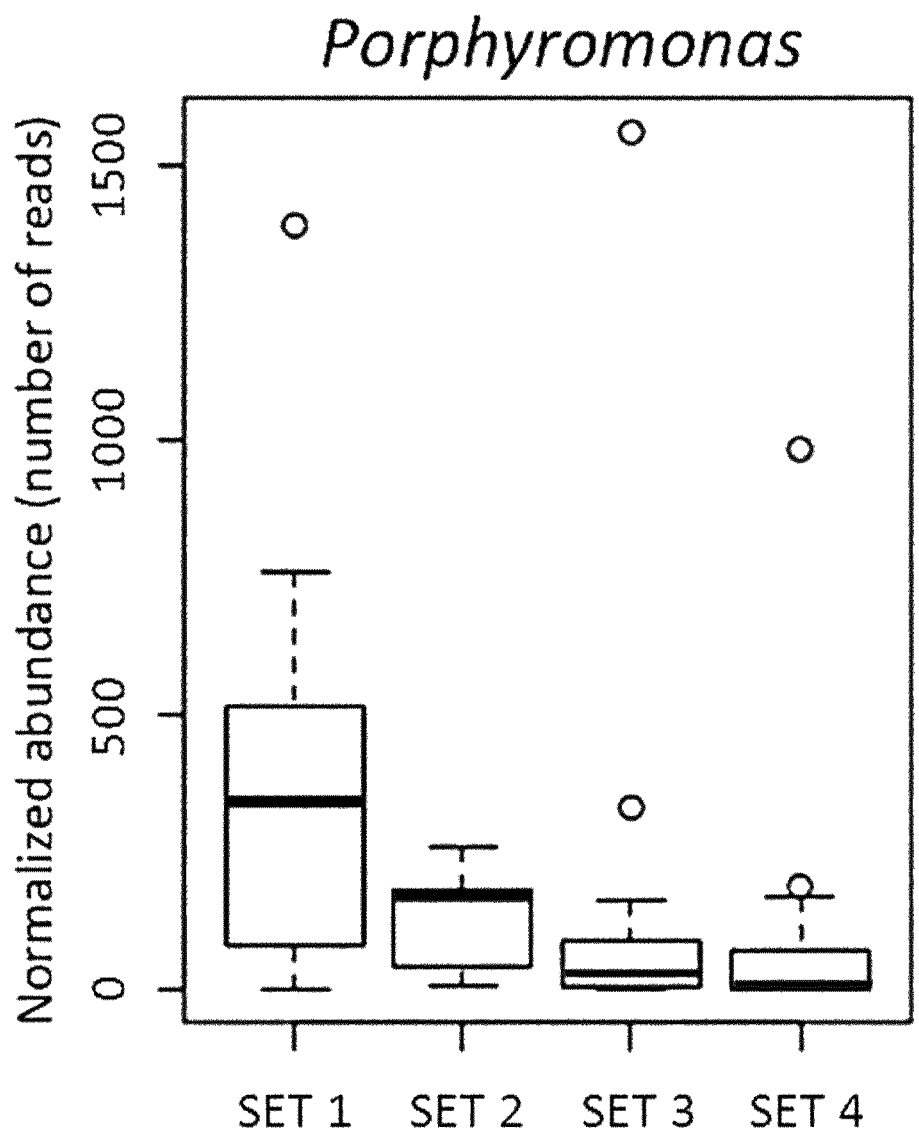
Figure 2C:
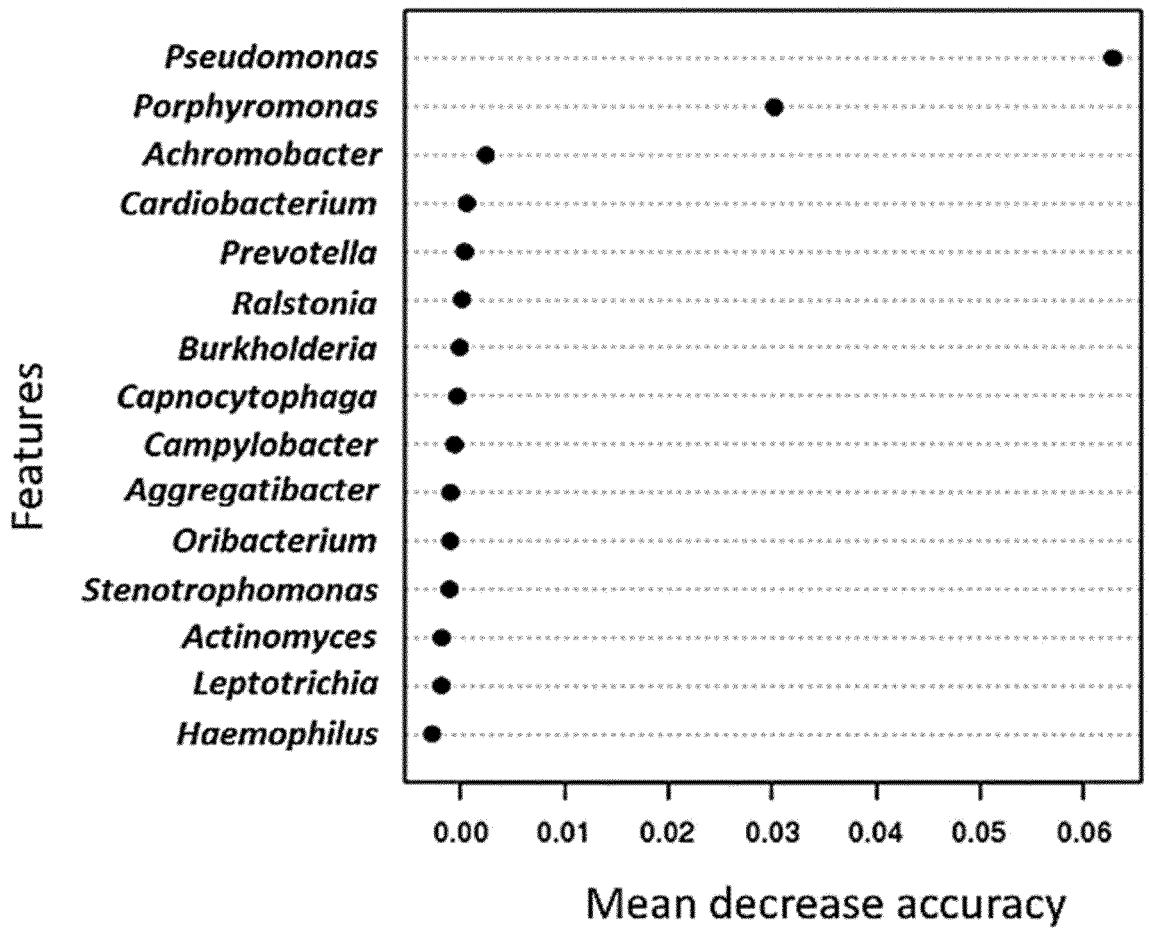

As expected, RA of *Pseudomonas* was significantly (p-value=1.79e$10^{-7}$) more abundant in samples from Group 1 (FIG. 2a). Interestingly, in group 1 patients who remained uninfected by *P. aeruginosa* during the follow-up, *Porphyromonas* RA at T0 was significantly higher (Mann-Whitney test, p-value<0.001) than in group 2 patients (FIG. 2b) with a mean RA of 252.9 reads for the group 1, and 130.7 reads for the group 2 (ratio of 1.9). At T0, patients from group 1 that will remain uninfected from *P. aeruginosa* exhibited 3-fold higher abundance of *Porphyromonas* compared to the 3 other groups (Group 1 T1, Group 2 T0 and T1). Moreover, those results were well supported by the observations of random forest (FIG. 2c) illustrated the significant connection between RA of *Pseudomonas* and *Porphyromonas*. Interestingly, *Porphyromonas* was more abundant in male group, which remained uninfected by *P. aeruginosa* illustrating the important potential role of this genus.

CF Airway Microbiota Clustered into Pulmotypes.
*Streptococcus*, *Haemophilus*, and *Staphylococcus*, Drivers of Three Pulmotypes.

The cohort samples clustered into 3 pulmotypes dominated either by *Streptococcus* (pulmotype A), *Haemophilus* (pulmotype B) or *Staphylococcus* (pulmotype C). This clustering was in agreement with the PCA results and was confirmed using Kruskal-Wallis test (p-value=0.001). Pulmotypes were driven by the variations in RA of these three dominant genera as well as other co-occurring genera. Indeed, pulmotype A was dominated by *Streptococcus* (30.0%), followed by *Neisseria* (13.3%), *Rothia* (9.2%), *Prevotella* (8.5%) and *Porphyromonas* (6.9%); pulmotype B by *Haemophilus* (62.0%), *Streptococcus* (9.5%) and *Aggregatibacter* (5.0%); and pulmotype C by *Staphylococcus* (54.6%), *Streptococcus* (13.5%) and *Neisseria* (6.7%). Overall, 69.2% (n=45), 15.4% (n=10) and 15.4% (n=10) of the sputum samples were assigned to pulmotype A, B and C, respectively. It is worth mentioning that the cytological score had no impact on clustering (Anosim test using Bray Curtis distance, p-value<0.05; $R^2$=0.073).

Pulmotypes exhibited different bacterial community structures (*Adonis* test using Bray Curtis distance, p-value=0.001) but did not differ in alpha-diversity, except for the H' where H' of pulmotype A (H': 3.39±0.83) was significantly (p-value=0.012) higher than H' of pulmotype C (H': 2.4±1.18)

Other parameters (such as patients' age, BETR categories, CFTR mutations, BMI) were tested to find a link between pulmotype but none of them reach the significance (data not shown).

We also observed important inter- and intra-pulmotype fluctuations. During the longitudinal follow-up, shifts of pulmotype were observed for 5 CF patients. Indeed, pulmotypes of patients 023 and 226 changed from pulmotype A to pulmotype C while the contrary was observed for patient 065. Patient 253 shifted from pulmotype A to B, in contrast to patient 076.

Association of Pulmotypes with CF Features.

We observed that *Porphyromonas* proportions were highly abundant in several samples belonging to the pulmotype A with a mean RA of 6.9% per sample (2.5% per sample for the pulmotype B, and 3.8% per sample for the pulmotype C in average) although these trends did not reach significance. Interestingly, viral communities did not significantly impact the pulmotype clustering (Kruskal-Wallis test, p-value>0.1). However, according to a g_test of independence, the presence of rhinovirus was correlated with 2 OTUs: the presence of *H. influenzae* and the absence of *P. aeruginosa* (p-value<0.05). Interestingly, 90% of samples (n=9 out of 10 samples) belonging to pulmotype C had a 'free' status according to Lee's criteria. In the 2 others pulmotypes, no relationship was observed with Lee's criteria. We also observed a significant lower prevalence of *Leptotrichia*, a male-biomarker, in pulmotype C compared to pulmotypes A and B (Kruskal Wallis test, p-value<0.01) (see SI results for details).

Discussion

This cohort study aimed at finding early biomarkers of *P. aeruginosa* colonization in CF. We made the hypothesis that the microbiota might be more or less permissive to *P. aeruginosa* in CF airways. To assess this hypothesis, we explored the characteristics of these microbiota including bacteria and viruses during the early stages of *P. aeruginosa* colonization. Surprisingly, instead of pathobionts, we identified signatures of CF lung at lower risk of *P. aeruginosa* infection and identified 3 pulmotypes potentially correlated to pulmonary disease progression.

At the stage of *P. aeruginosa* chronic infection, a low bacterial diversity has been positively correlated with CF progression and presence of *P. aeruginosa*. In the present cohort, mostly composed of CF children not chronically infected with *P. aeruginosa*, the acquisition of *P. aeruginosa* did not decrease alpha-diversity indices over the 8 months follow-up. Consequently, other biomarkers were searched. *Porphyromonas* RA was significantly higher in patients from group 1 (patients who remained uninfected for *P. aeruginosa*) than patients from group 2 (p-value<0.001). Conversely, patients harboring *Porphyromonas* RA below the threshold of 5.33%, showed 3.7-fold risk of acquiring *P. aeruginosa*. Bacteria from the *Porphyromonas* genus are anaerobic commensals of the oral microbiota and also considered as part of the CF pulmonary core microbiota. In a previous study of our team (Héry-Arnaud G (2015) Impact of the CFTR-potentiator ivacaftor on airway in cystic fibrosis patients carrying a G551D mutation. PLoS One 10(4): e0124124) that aimed at characterizing the impact of the CFTR potentiator drug (ivacaftor) on CF airway microbiota, we demonstrated a sustainable increase of *Porphyromonas* RA after initiation of the treatment which was positively correlated with the percentage of predicted forced expiratory volume in 1 second (FEV-1). Taking together these results suggest that *Porphyromonas* could be a favorable prognostic biomarker in CF. This finding also raises the question about the link between this bacterium and the *P. aeruginosa*-negative phenotype. In vitro experiments should be performed to study the interaction between *Porphyromonas* and *P. aeruginosa* in order to confirm the possible favorable role of this anaerobic bacterium in the CF respiratory tract, even if, as such, one bacterial genus cannot fully explain the stability of CF progression.

Beyond pathogens, host factors shape the composition of the airway microbiota within the mucus-microbe-host crosstalk. We found that the gender impacted the composition of the CF airway microbiota. The gender gap in life expectancy of CF patients has been documented for years in United States and European countries (Jain R (2014) Gender differences in outcomes of patients with cystic fibrosis. J Women's Health 23(12):1012-1020). Despite tremendous improvements in healthcare and treatment, females with CF still have worse outcome than males, with a higher rate of mortality, a younger age for *P. aeruginosa* colonization, and a higher risk of non-mucoid to mucoid conversion of *P. aeruginosa*. Likewise, gender gap has been stated in other pulmonary diseases. Sexual dimorphism of the immune response may be responsible for gender differences in such pulmonary diseases. Sex hormones may also have an effect on lung function; for example, estrogen was shown to induce *P. aeruginosa* mucoid phenotype (McElvaney N G (2012) Effect of estrogen on *Pseudomonas* mucoidy and exacerbations in cystic fibrosis. NEJM 366(21):1978-1986). However, the fact that the gap gender is objectivized before puberty and after menopause implies that hormones might be an incomplete explanation. It was recently hypothesized that the respiratory status was the most important factor in CF gender gap, given that respiratory infections were the larger contributor to morbidity and mortality. Thus, the present study provides a missing link between gender disparity and infection susceptibility (which may concern a wide range of pathogens and not only *P. aeruginosa*). This is also the first time that a microbiome study corroborates epidemiological studies in which the CF gender gap is highlighted. We identified an overrepresentation of *Selenomonas*, *Leptotrichia*, *Atopobium*, *Parvimonas* and *Bifidobacterium* in the male group, which are obligate anaerobic bacteria and previously related to a healthy state (Martinez F J, for the COMET investigators (2014) Lung microbiome and disease progression in idiopathic pulmonary fibrosis: an analysis of the COMET study. Lancet Respir Med 2:548-556). We might hypothesize that these male-associated genera and *Porphyromonas* may contribute as a protective barrier against *P. aeruginosa* in CF patients of male gender in particular. In vitro and in vivo analyses are needed to confirm this hypothesis. *Leptotrichia* was found to be dominant in healthy oral communities. A study observed that the RA of *Actinobacteria* (Atopobium's phylum) was negatively correlated with *P. aeruginosa* suggesting a direct impact of the resident microbiota on a bacterial pathogen through a competition for similar ecological niche and behavior. In males, *Bifidobacterium* was found in low abundance (RA<0.1%), while it was totally absent in females. Other study demonstrated that a decrease of *Bifidobacterium* was associated with an asthma phenotype. These four bacterial genera are also usually described as gut-living bacteria and found in patients with chronic obstructive pulmonary disease. Recently, the gut-lung connection has been revealed in CF, where the respiratory tract colonization was found to be presaged by the gut colonization, and where the composition of the gut microbiota in CF in early life was directly implicated in pulmonary disease progression.

The samples strongly clustered into three pulmotypes, a major one dominated by *Streptococcus* (pulmotype A), and two other ones dominated either by *Haemophilus* (pulmotype B) or *Staphylococcus* (pulmotype C). In a previous study where cohorts of children and adults were pooled, 2 'ecotypes' were detected represented either by *P. aeruginosa* or *Streptococcus* (Dalpke A H (2015) Comparison of microbiomes from different niches of upper and lower airways in children and adolescents with cystic fibrosis. PLoS One 10(1):e0116029). Here, pulmotype A was characterized by the highest Shannon diversity. The dominance of *Streptococcus* has already been correlated with a high bacterial diversity, an increased respiratory function, and the earliest months of CF patients' life. The early establishment of the *Streptococcus* group in the respiratory tract has also been viewed as a favorable biomarker in CF progression, acting directly and positively in the acquisition model of CF pathogens, more particularly *P. aeruginosa*. *Streptococcus* species could thus be defined as foundation species whose initial and persistent colonization is a favorable signature in CF. In addition, *Streptococcus* from the *salivarius* group were positively correlated with increased FEV-1. Interestingly, we also observed that *Porphyromonas* was significantly more prevalent in samples belonging to pulmotype A.

*Haemophilus* was the main contributor of pulmotype B. *H. influenzae* and *P. aeruginosa* are under a strong interspecific competition to colonize the CF airway microbiota. Even though the studied cohort was mostly composed of *P. aeruginosa*-negative patients, we observed indeed that *Haemophilus* had a strong impact on the CF airway microbiota structure. Moreover, *Haemophilus* was more abundant in rhinovirus-positive samples, which in turn harbored low RA of *P. aeruginosa*. Based on this observation, we can hypothesize that pulmotype B appeared after pulmotype A following a microbiota perturbation such as antibiotherapy initiation of or viral infection.

*H. influenzae* and *S. aureus* are considered the most prevalent pathogens in pediatric CF population, being later gradually replaced by *P. aeruginosa*. Interestingly, the last pulmotype defined by cluster analysis was driven by *Staphylococcus* and might be considered as a pathotype considering that its driver is a well-characterized pathogen. In early stages of CF, high RA of *S. aureus* was positively associated with an increased airway inflammation. Moreover, *S. aureus* colonization is considered as a risk factor for *P. aeruginosa* initial colonization. Ninety percent of pulmotype C samples corresponded to patients with *P. aeruginosa* 'free' status, in other words patients who were in a more advanced state of pulmonary infection than 'Never' patients.

Finally, we investigated the association between pulmotypes and CF progression. During the longitudinal follow-up, pulmotype shifts were only observed for 5 CF patients. These observations indicated a relative stability of the CF airway microbiota over time in childhood. For patient 023, who shifted from pulmotype A to pulmotype C, a dramatic loss of FEV-1 (from 76.2 to 60.5% in only 3 months; data not shown) was observed. For further longitudinal studies, it would be interesting to follow microbiome long-term evolution and associated pulmotypes to define precisely their kinetic throughout the disease history. Such a study would allow to evaluate whether pulmotype shifts (e.g. from A to C) are deleterious for the respiratory function and can be correlated with the clinical state. We hypothesize that the pulmotype "*Streptococcus*" represents the microbiome funder pulmotype of a stable CF lung; its boundaries are less delimited in terms of species composition and harbors a high diversity, synonymous of a healthy respiratory state. Because it may be inappropriate to talk about 'healthy lung' in the CF context, we propose to define the shift from pulmotype A to another pulmotype as a major microbial dysbiosis of the CF lung. Pulmotypes "*Haemophilus*", "*Staphylococcus*" (and "*Pseudomonas*" in adults) would correspond to the entrance in a perturbed CF ecosystem, and thus defined as pathotype.

CONCLUSION

This study showed the crucial importance of microbiota data in the management of CF patients. The pulmotype concept is a possible way to simplify the complexity of the CF airway microbiota which was previously defined as polymicrobial and spatially heterogeneous. Using this concept, we could identify signatures that could be useful in predicting the CF progression. Identification of bacteria of interest opens the possibility of using them as prognostic biomarkers for the identification of new treatment options. Further cohort studies are needed to validate these findings, and to address the question of causality.

The influence of the input microbiota on CF progression during early life has also to be investigated. In the not-too-distant future, study of both biochemical and microbial signatures will constitute new approaches to understand CF microbiology.

REFERENCES

Throughout this application, various references describe the state of the art to which this invention pertains. The disclosures of these references are hereby incorporated by reference into the present disclosure.

The invention claimed is:

1. A method for treating pulmonary colonization or infection by *Pseudomonas aeruginosa* in a subject suffering from cystic fibrosis (CF) comprising:
Measuring, using 16S rRNA deep-sequencing, the relative abundance of all *Porphyromonas* genus bacteria in a biological sample obtained from said subject, wherein the biological sample is bronchoalveolar lavage (BAL) or sputum or protected specimen brushing from bronchoscopic sampling or pharyngeal swabs, the relative abundance of *Porphyromonas* genus bacteria being the percent composition of *Porphyromonas* genus bacteria relative to the total number of bacteria genus in said biological sample;
determining that the measured relative abundance of *Porphyromonas* genus bacteria is less than 5.33% and thus that the biological sample has a low relative abundance of *Porphyromonas* genus bacteria as compared to a corresponding biological sample obtained from an uninfected subject which is indicative of a high risk of developing pulmonary colonization/infection by *Pseudomonas aeruginosa*; and then
administering to the subject a therapeutically effective amount of *P. aeruginosa* specific antibiotics.

2. The method according to claim 1 wherein the subject is a child.

3. The method according to claim 1 wherein the biological sample is bronchoalveolar lavage (BAL) or sputum.

4. A method of preventing or reducing pulmonary colonization or infection by *P. aeruginosa* in a subject suffering from cystic fibrosis (CF) comprising:
measuring, using 16S rRNA deep-sequencing, the relative abundance of all *Porphyromonas* genus bacteria in a biological sample obtained from said subject, wherein the biological sample is bronchoalveolar lavage (BAL) or sputum or protected specimen brushing from bronchoscopic sampling or pharyngeal swabs, the relative abundance of *Porphyromonas* genus bacteria being the percent composition of *Porphyromonas* genus bacteria relative to the total number of bacteria genus in said biological sample;
determining that the measured relative abundance of *Porphyromonas* genus bacteria is less than 5.33% and thus that the biological sample has a low relative abundance of *Porphyromonas* genus bacteria as compared to a corresponding biological sample obtained from an uninfected subject which is indicative of a high risk of developing pulmonary colonization/infection by *Pseudomonas aeruginosa*; and then
administering to the subject a therapeutically effective amount of *P. aeruginosa* specific antibiotics.

* * * * *